(12) United States Patent  (10) Patent No.: US 9,316,623 B2
Seo et al.  (45) Date of Patent: Apr. 19, 2016

(54) MICRO-SCALE PASSIVE VAPOR PRECONCENTRATOR/INJECTOR

(71) Applicant: The Regents of the University of Michigan, Ann Arbor, MI (US)

(72) Inventors: Jung Hwan Seo, Ann Arbor, MI (US); Sun Kyu Kim, Ann Arbor, MI (US); Edward T. Zellers, Ann Arbor, MI (US); Katsuo Kurabayashi, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 561 days.

(21) Appl. No.: 13/747,120

(22) Filed: Jan. 22, 2013

(65) Prior Publication Data

US 2013/0186174 A1 Jul. 25, 2013

Related U.S. Application Data

(60) Provisional application No. 61/589,040, filed on Jan. 20, 2012.

(51) Int. Cl.
G01N 1/22 (2006.01)
G01N 30/00 (2006.01)
F16L 53/00 (2006.01)
G01N 25/00 (2006.01)
G01N 1/40 (2006.01)
G01N 30/08 (2006.01)

(52) U.S. Cl.
CPC ............... *G01N 30/00* (2013.01); *F16L 53/00* (2013.01); *G01N 1/405* (2013.01); *G01N 25/00* (2013.01); *G01N 30/08* (2013.01); *Y10T 137/6416* (2015.04)

(58) Field of Classification Search
None
See application file for complete search history.

(56) References Cited

U.S. PATENT DOCUMENTS

| | | | | |
|---|---|---|---|---|
| 3,985,017 A | * | 10/1976 | Goldsmith | 436/116 |
| 4,759,210 A | * | 7/1988 | Wohltjen | 73/31.07 |
| 4,780,282 A | * | 10/1988 | Holtzclaw et al. | 422/401 |
| 5,517,866 A | * | 5/1996 | Manning et al. | 73/863.21 |
| 7,615,189 B2 | | 11/2009 | Aslam et al. | |
| 2003/0175947 A1 | * | 9/2003 | Liu et al. | 435/288.5 |

(Continued)

OTHER PUBLICATIONS

Seo, Jung Hwan et al. "Microfabricated Integrated Sampler-Injector (MISI) for Micro Gas Chromatography." MEMS 2011. IEEE Conference. Publication Date: Jun. 23-27, 2011.
Seo, Jung Hwan et al. "Effect of Thermal Desorption Kinetics on Vapor Injectio Peak Irregularities by a Microscale Gas Chromatography Preconcentrator." Analytical Chemistry. vol. 84. pp. 6336-6340. (2012).

*Primary Examiner* — Hezron E Williams
*Assistant Examiner* — Truong Phan
(74) *Attorney, Agent, or Firm* — Harness, Dickey & Pierce, PLC

(57) ABSTRACT

A passive and reusable preconcentrator/injector device for measuring gas-phase analytes and methods of use. The device includes an upper plate defining an array of micro-scale diffusion channels and a lower plate secured to the upper plate. The lower plate defines a cavity for a reusable collection material in fluid communication with the micro-scale diffusion channels. An integral heating unit is provided adjacent the lower plate and configured for heating the cavity. A loading port may be included for introducing the reusable collection material into the cavity. An inlet port and an outlet port are provided, both in fluid communication with the cavity. The device may include a fluidic manifold system comprising a plurality of conduits disposed between the adsorbent cavity and the outlet port.

25 Claims, 14 Drawing Sheets

(56) References Cited

U.S. PATENT DOCUMENTS

| | | | |
|---|---|---|---|
| 2003/0235515 A1* | 12/2003 | Fike | 422/69 |
| 2006/0094118 A1* | 5/2006 | Tipler et al. | 436/43 |
| 2009/0246883 A1* | 10/2009 | McBrady et al. | 436/164 |
| 2011/0010107 A1* | 1/2011 | Fedder et al. | 702/22 |

* cited by examiner

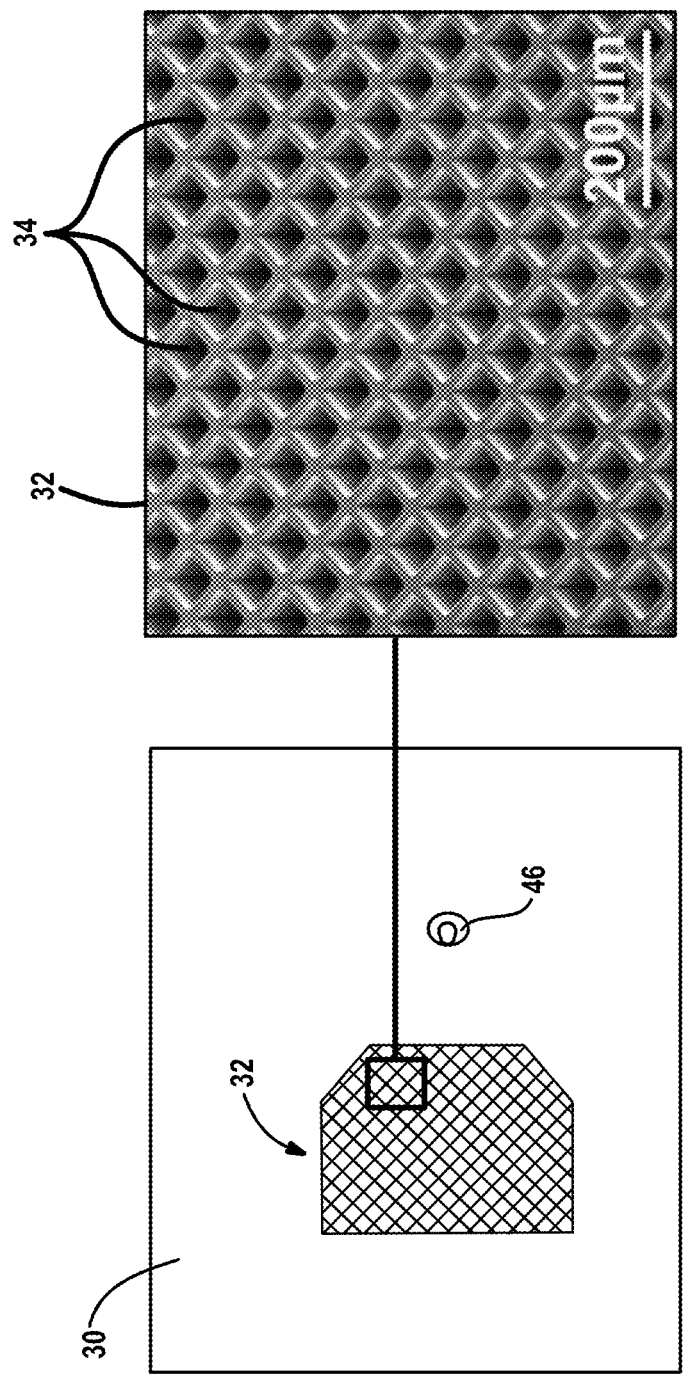

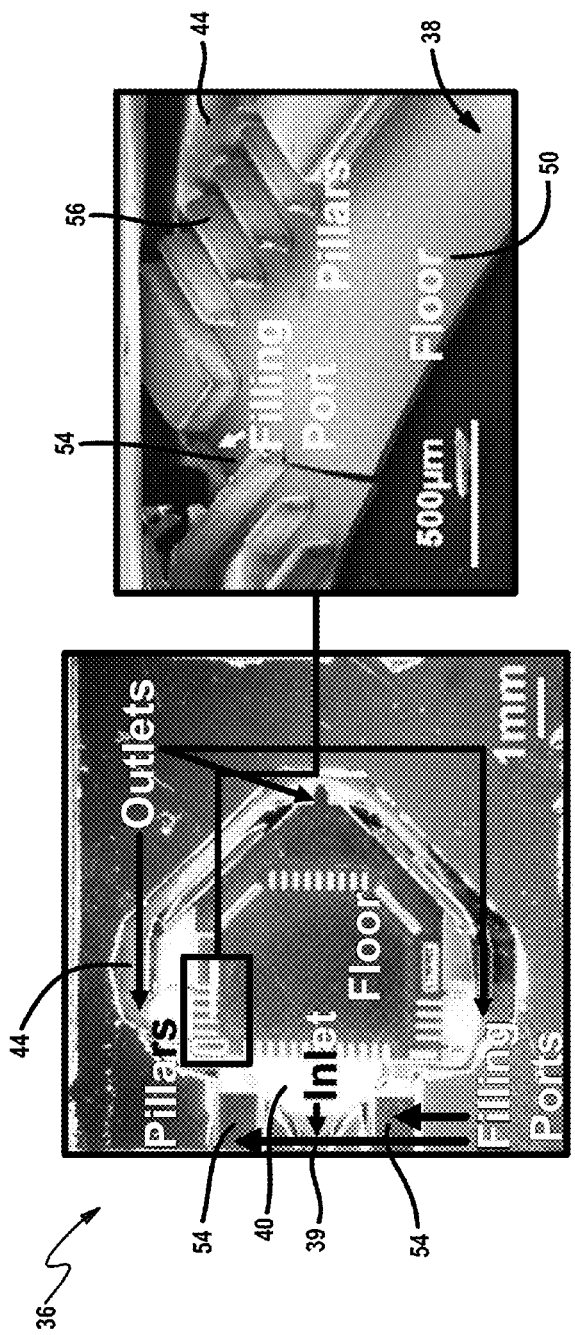
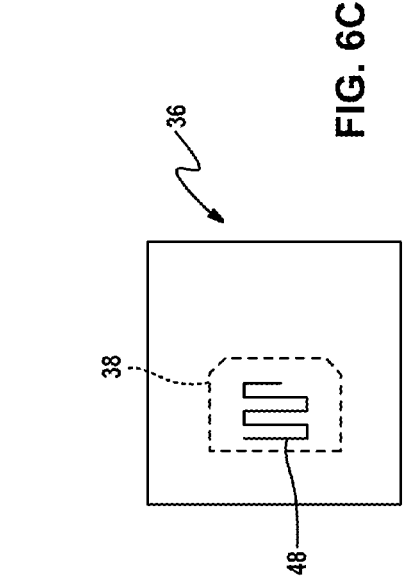
FIG. 6B
FIG. 6C
FIG. 6A

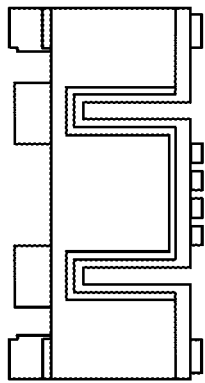
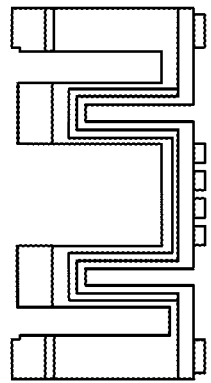
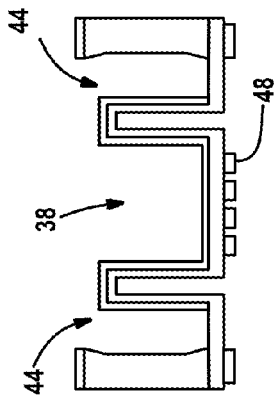
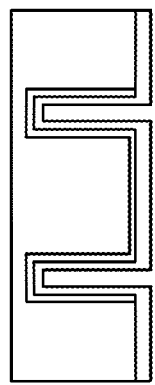
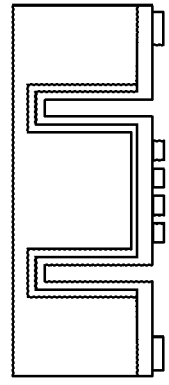
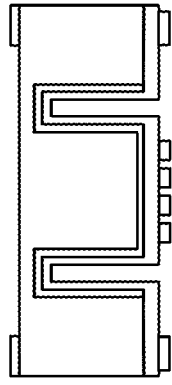
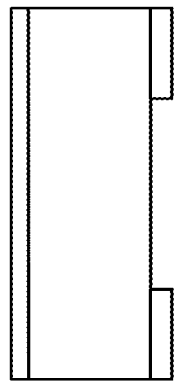
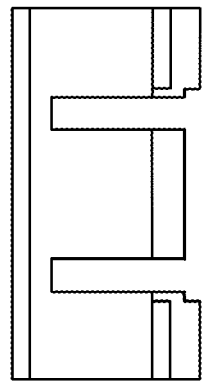
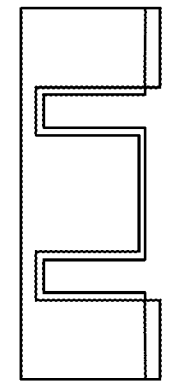
FIG. 10A

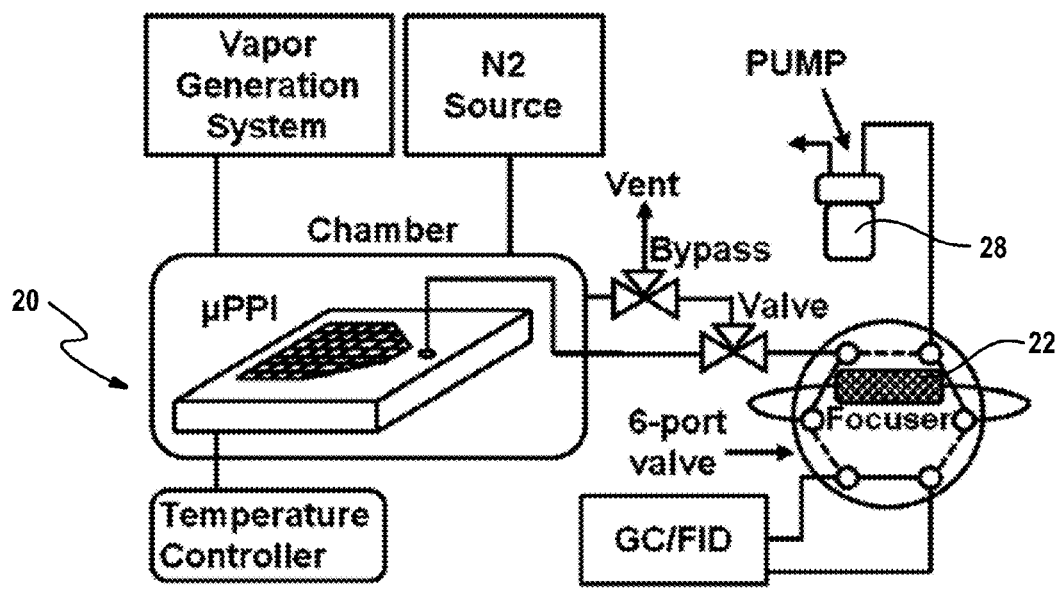
FIG. 11A
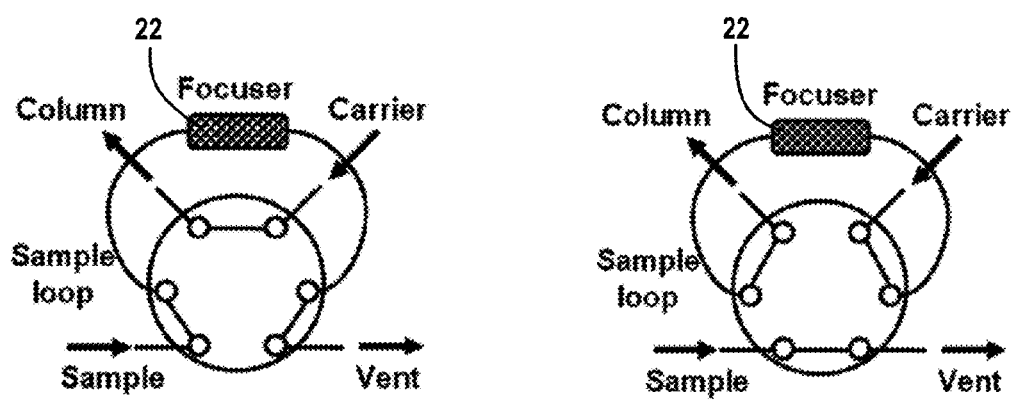
FIG. 11B  FIG. 11C

MICRO-SCALE PASSIVE VAPOR PRECONCENTRATOR/INJECTOR

CROSS-REFERENCE TO RELATED APPLICATIONS

This application claims the benefit of U.S. Provisional Application No. 61/589,040, filed on Jan. 20, 2012. The entire disclosure of the above application is incorporated herein by reference in its entirety.

GOVERNMENT RIGHTS

This invention was made with government support under ERC-9986866 awarded by the National Science Foundation. The government has certain rights in the invention.

FIELD

The present disclosure relates to micro-scale VOC collection, and more specifically to passive vapor preconcentrator and injector structures, including applications and fabrications of the same.

BACKGROUND AND SUMMARY

This section provides background information related to the present disclosure which is not necessarily prior art. This section also provides a general summary of the disclosure, and is not a comprehensive disclosure of its full scope or all of its features.

Gas chromatographic microsystems (μGCs) offer the potential for analyzing mixtures of volatile organic compounds (VOCs) in miniature packages suitable for personal exposure monitoring, point-of-care medical diagnostics, explosive detection, and other applications. Typical μGCs may include an accumulator, a sample injector, a separation column, and a detector, each of which may be fabricated from Si, glass, or other suitable materials, and are generally provided as separate devices or components.

It may be necessary, however, to concentrate the VOC(s) of interest prior to analysis because detectors may lack the inherent sensitivity required to attain the low detection limits demanded in many applications. For this reason, μGC injectors may incorporate a preconcentration function and may include a device with an internal cavity packed or lined with an adsorbent material. The VOCs in an air sample, drawn through the device by means of a small pump, are trapped on the surface of a generally high-surface-area solid adsorbent. Subsequent rapid heating leads to desorption into a carrier gas flowing at a lower rate, which leads to an enhancement in concentration of the VOCs that are passed downstream to a measurement device such as a separation microcolumn and/or a microsensor or microsensor array.

One factor that may affect performance is the dynamic adsorption capacity, which is related to the volatility and functionality of the VOC(s), the mass and specific surface area of the adsorbent (and therefore the size/mass of the device), and the flow rate of the air sample being drawn through the device. Other performance factors may include the desorption rate, efficiency, and bandwidth, which are also related to the volatility and functionality of the VOC(s), the mass and surface area of the adsorbent, and the desorption/injection flow rate, as well as the maximum temperature and rate at which the device is heated. Power requirements may also be a concern, and often have a significant influence on device design.

As progress is made toward smaller and more power efficient components, the power required for pumping becomes more significant. For example, most μGC systems rely on commercial mini-pumps, which dissipate on the order of 1 W-4 W. Depending on the required sample volume and the time of analysis, the energy for pumping may exceed that for the other power-intensive components.

It is desirable for VOC samplers to be small (i.e., a few cubic centimeters), employ carbon based trapping materials, and have sampling rates of about 3 to 30 mL/min. With known devices, following the sample collection period, typically 4-24 hours of using a pump device to collect the sample, the device is returned to the laboratory for solvent or thermal desorption followed by conventional measurement analysis. There remains a need for even smaller samplers, and samplers that are more convenient to use with little or no energy consumption during collection.

The present technology provides a passive preconcentrator and injector device. The device may include an upper portion defining an array of micro-scale diffusion channels, and a lower portion defining a cavity in fluid communication with the micro-scale diffusion channels. A collection material may be disposed within the cavity and configured to capture at least one gas-phase analyte. An integral heating unit may be disposed in thermal communication with the lower portion and configured to heat the cavity. An inlet port and an outlet port may be provided in fluid communication with the cavity. The device may be configured to collect at least one compound in a gas phase at a known rate by using passive diffusion, without the use of artificial circulation, and subsequently remove the compound for injection to a measuring device.

According to various aspects of the present technology, the passive preconcentrator and injector device may include an upper plate defining an array of micro-scale diffusion channels, and a lower plate secured to the upper plate and defining a cavity in fluid communication with the micro-scale diffusion channels. An integral heating unit may be disposed on an exterior region of the lower plate and configured for heating the cavity. A loading port may be provided for introducing a reusable collection material, and an inlet port and an outlet port may be provided, both in fluid communication with the cavity. A fluidic manifold system comprising a plurality of conduits may be disposed between the cavity and the outlet port.

The present technology also provides a method of detecting a compound in the gas phase using a combination preconcentrator and injector device. The method comprises providing a passive preconcentrator and injector device including an upper portion defining an array of micro-scale diffusion channels, a lower portion defining a cavity in fluid communication with the micro-scale diffusion channels and containing a collection material, an integral heating unit, an inlet, and an outlet. The preconcentrator and injector device is exposed to a sampling area and the method allows for the collection material to passively capture a gas-phase analyte sample for a predetermined time period at a predetermined rate. The method includes connecting the outlet to a measurement device and actuating the integral heating unit and initiating thermal desorption to generate a desorbed gas or vapor. A desorbed gas or vapor is collected and analyzed to detect at least one captured or desorbed compound.

Further areas of applicability will become apparent from the drawings and description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 5A-5B illustrate detailed views of the top layer of the micro-scale passive vapor preconcentrator/injector device;

FIGS. 6A-6C illustrate detailed views of the bottom layer of the micro-scale passive vapor preconcentrator/injector device;

FIGS. 10A-10I illustrate an exemplary fabrication process for the bottom layer of micro-scale passive vapor preconcentrator/injector device according to various aspects of the present technology;

FIG. 11A is a schematic of a test setup useful to characterize a sampling rate of a micro-scale passive vapor preconcentrator/injector device according to various aspects of the present technology, FIG. 11B illustrates a vapor sample being transferred to a focuser, and FIG. 11C illustrates, when a valve is switched, the vapor sample in the focuser being thermally injected onto a column;

Figure 12A:
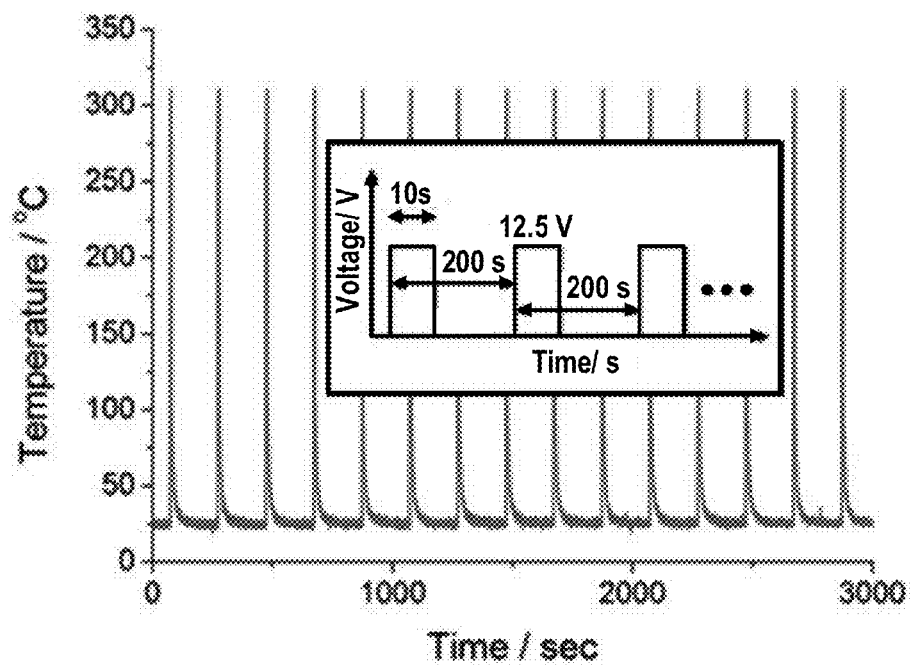
Figure 12B:
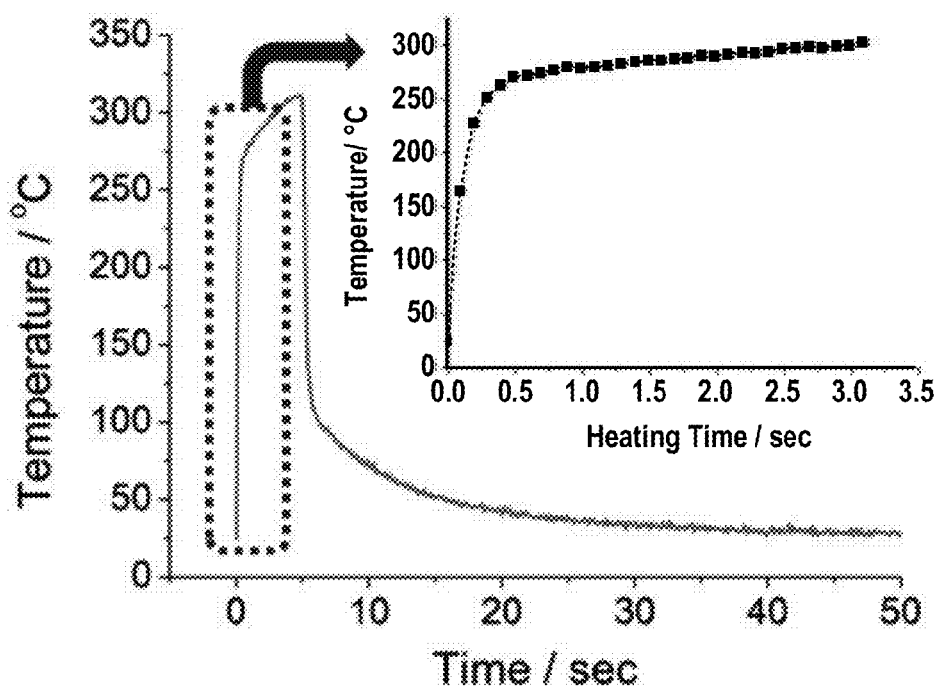
Figure 13:
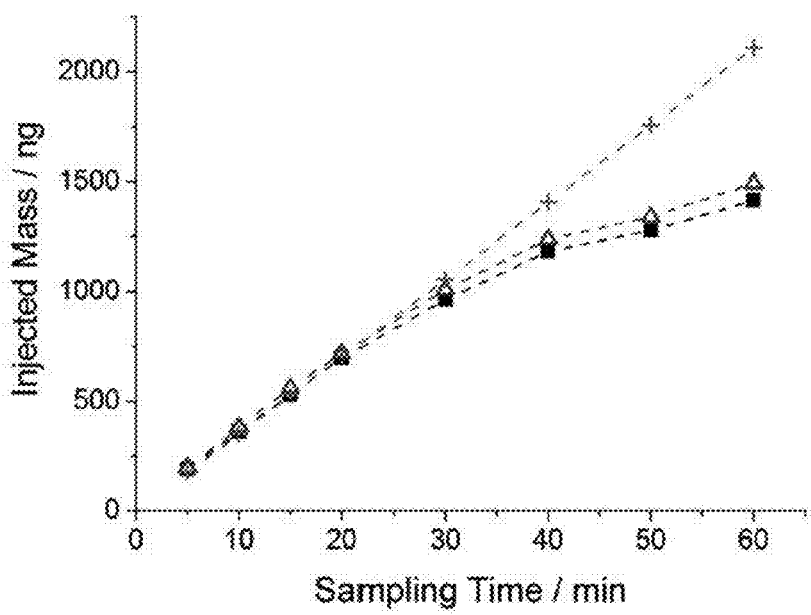
Figure 14:
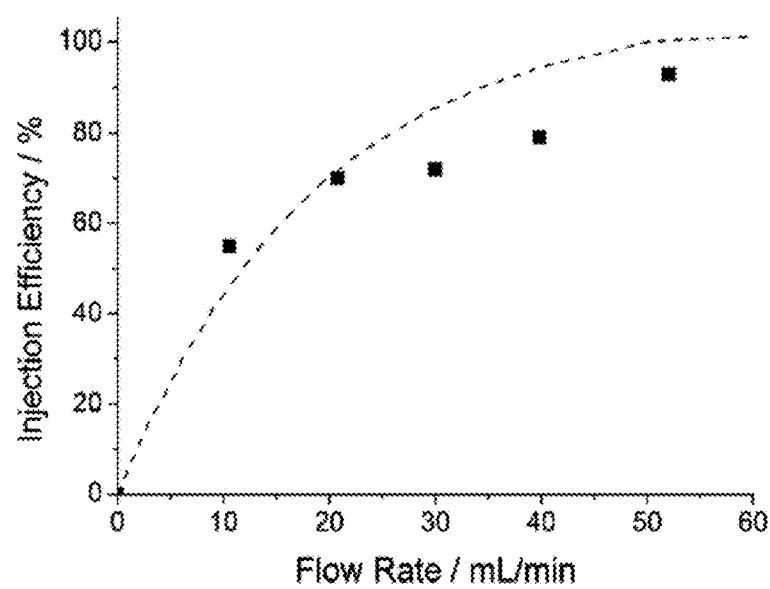
Figure 15A:
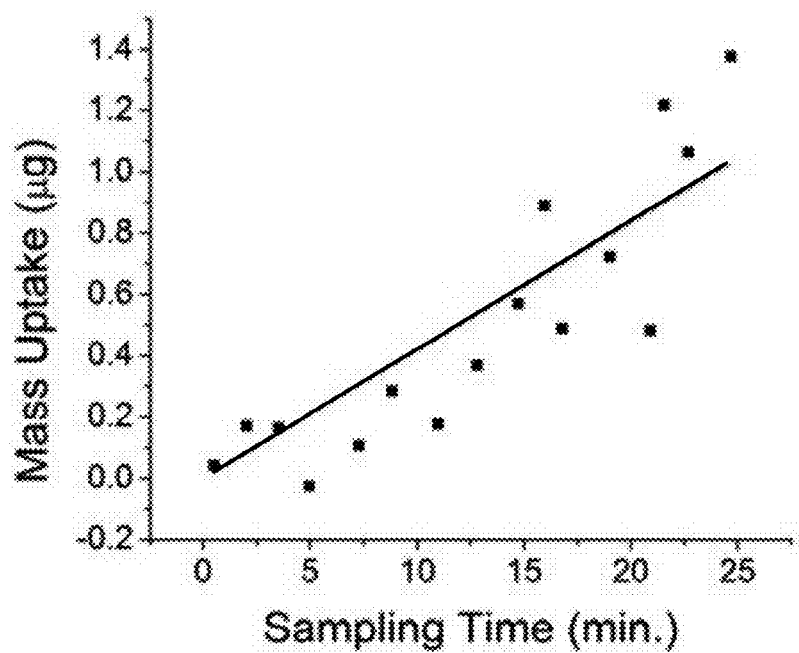
Figure 15B:
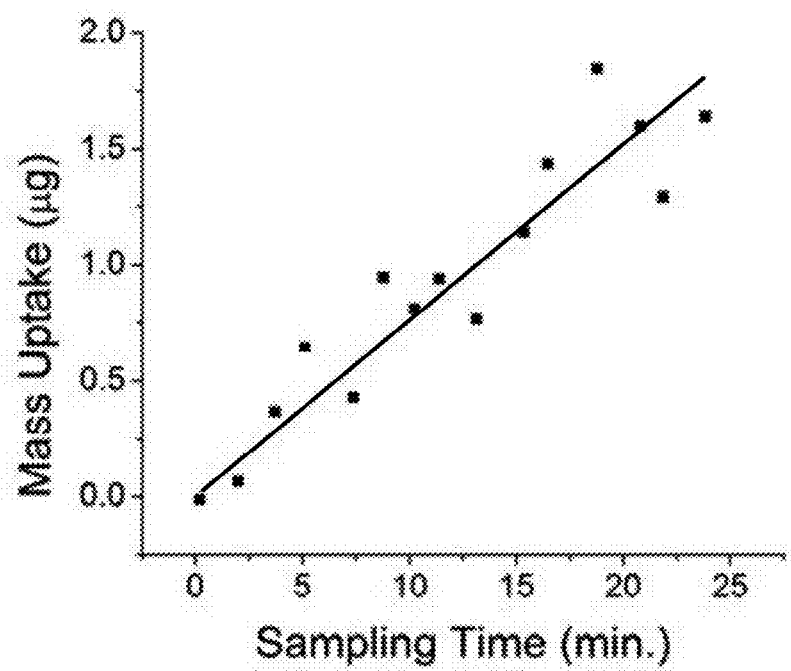

FIGS. 12A and 12B graphically illustrate a thermal response of the micro-scale passive vapor preconcentrator/injector device with a power input of about 1 W;

FIG. 13 graphically illustrates plots of the mass of toluene captured and desorbed as a function of sampling time for the micro-scale passive vapor preconcentrator/injector device according to various aspects of the present technology;

FIG. 14 graphically illustrates modeled and experimental values of capture/transfer injection efficiency versus suction flow rate for the micro-scale passive vapor preconcentrator/injector device according to various aspects of the present technology; and FIGS. 15A-15B illustrate the mass uptake rates measured by thermal gravimetric analysis (TGA) for toluene concentrations of 1.2 ppm and 1.7 ppm, respectively using a micro-scale passive vapor preconcentrator/injector device according to various aspects of the present technology.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Throughout this disclosure, the numerical values represent approximate measures or limits to ranges to encompass minor deviations from the given values and embodiments having about the value mentioned as well as those having exactly the value mentioned. Other than in the working examples provides at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

Figure 1:
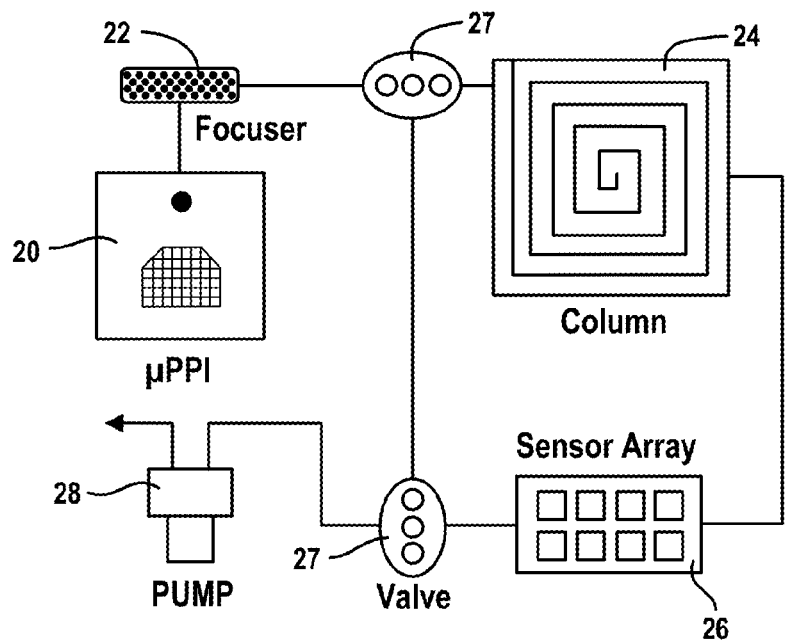
FIG. 1 is schematic layout of a micro-scale gas chromatograph system according to various aspects of the present technology.
Figure 2A:
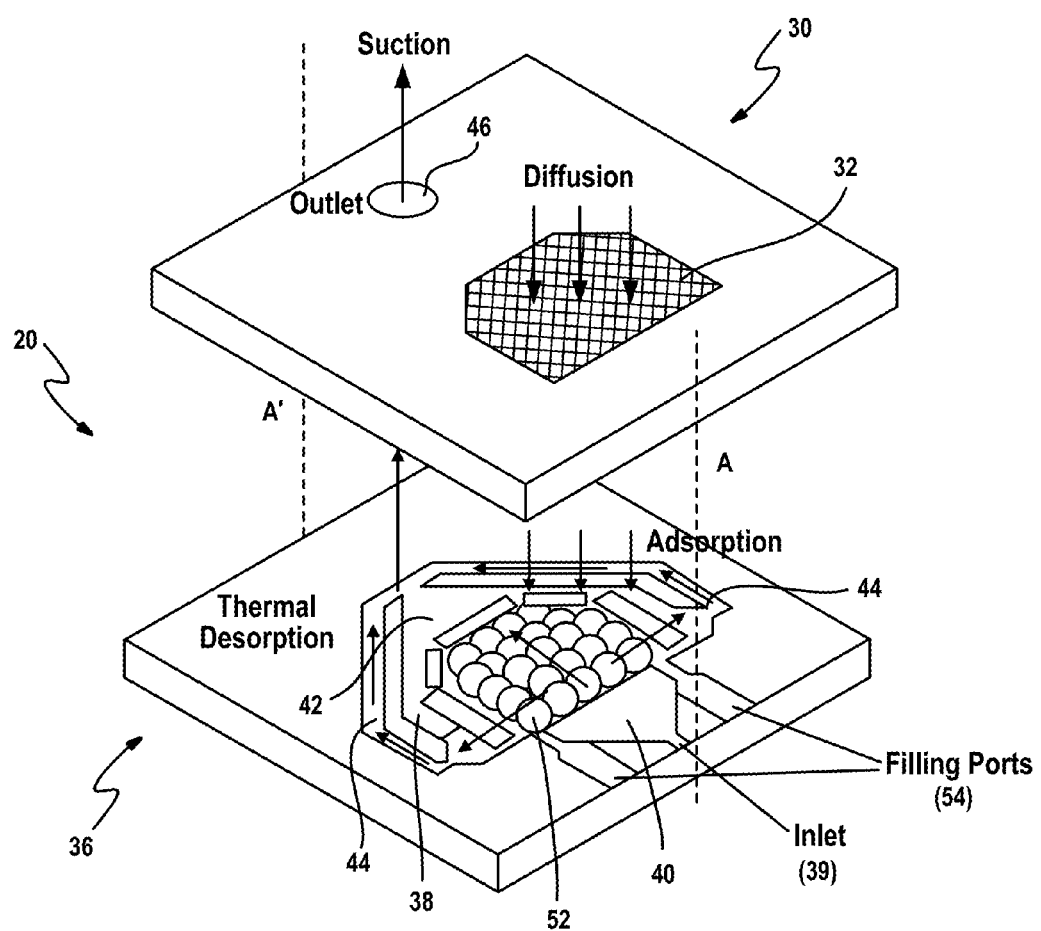
FIGS. 2A and 2B are exploded perspective view of a micro-scale passive vapor preconcentrator/injector device according to various aspects of the present technology.
Figure 2B:
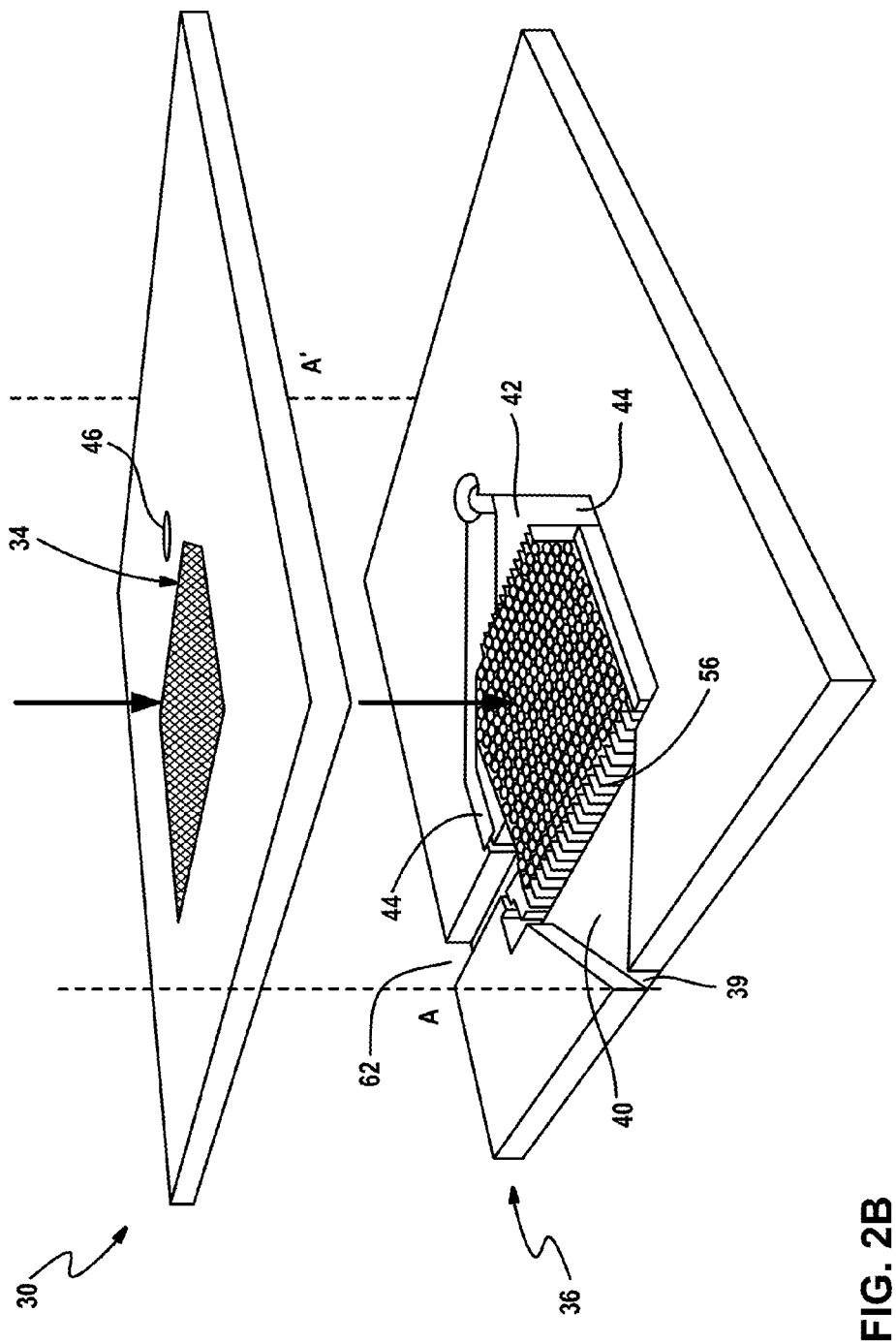

In various aspects, the present teachings provide the design, fabrication, and methods for use of a micro-scale, or micro-machined, passive vapor preconcentrator/injector device. FIG. 1 is schematic layout of a micro-scale gas chromatograph system and FIGS. 2A and 2B are exploded perspective views of a micro-scale passive vapor preconcentrator/injector device 20 according to the present teachings. Intended for incorporation with various measuring devices, for example, a gas chromatographic microsystem (μGC) for analyzing organic vapor mixtures, the preconcentrator/injector device 20 captures gas and/or compounds in vapors from the air at a known rate by means of passive diffusion and collection techniques. As used herein, the term "passive" means that the diffusion generally takes places without active or artificial circulation, such as using a pump or pumping means, to circulate an air sample. With renewed reference to FIG. 1, after the preconcentrator/injector device 20 has been exposed to a sampling area for a sufficient time, a vapor sample may be thermally desorbed (or otherwise removed from the device) using an integral heater and transferred, for example via a valve 27 and pump 28 arrangement, to a focuser 22 for injection downstream to a microcolumn 24 ultimately for the separation and detection by an array of sensors and/or micro sensors 26. In other aspects, for example, if a reagent type collection mechanism is used, further chemical treatment may be performed, such as solvent mixing to remove the collected compounds and/or analytes for further analysis.

In certain situations, it may be desirable to obtain a collection or a plurality of different samples and/or compounds. Thus, in various aspects, the present technology may also relate to the use of a plurality of devices 20 together. One device may include a plurality of cavities and a plurality of grids with micro-scale diffusion channels arrays in respective fluid communication with one another. In other aspects, a plurality of devices can be used together, where each may be configured to independently sample different gas-phase analytes or collect different compounds in one or more gas-phase analytes, either simultaneously or at different times. The separate devices or cavities may include different collection materials, and may be provided with different geometries permitting different sampling rates, as will be discussed below.

With reference to FIGS. 1-6, the passive preconcentrator/injector device 20 may include a two-layer structure provided with a top layer 30, also referred to as a top portion or top plate, including a grid 32 of precisely defined micro-scale diffusion channels 34 through which a gas-phase analyte containing VOCs or other compounds can diffuse, and a bottom layer 36, also referred to as a bottom portion or plate, with a cavity 38 that may be thermally isolated from other components. The two layers may be secured to one another as is known in the art. The cavity 38 may be suitably sized to retain a collection material 52, such as an adsorbent or reagent, for the collection of compound(s) in a gas-phase analyte sample. In various aspects, the collection material 52 is reusable. In certain aspects, a collection material can be grown in the cavity, such as the nanotubes disclosed in U.S. Pat. No. 7,615,189 issued to Aslam et al. on Nov. 10, 2009, which is incorporated by reference in its entirety herein. The bottom plate 36 may include an inlet port 39 adjacent an inlet area 40, and an outlet area 42 in fluid communication with an outlet port 46.

In various aspects, the grid 32 or each of the array of micro-scale diffusion channels 34 comprises an aperture and depth such that the total number of channels 34 is sufficient to provide a predetermined and finite sampling rate. By way of example only, the sampling rate may be from about 0.1 to about 30 mL/min, from about 0.2 to about 20 mL/min, from about 2 to about 10 mL/min, or from about 5 to about 8 mL/min. It should be understood to those skilled in the art that the sampling rate may vary based on a number of different variables, including diffusion coefficients for vapors. Thus, in various aspects the sampling rate may be compound-specific and the geometry of the channels 34 can be designed accordingly. In certain aspects, a ratio of the channel depth to the channel diameter may be greater than about 2, greater than about 2.5, or greater than about 3. Such a ratio may minimize any interference from ambient wind turbulence or other movement related to the sampling rate.

A fluidic manifold system may be provided with various conduits 44 and associated ports appropriately located throughout the preconcentrator/injector device 20, providing fluid communication between the cavity 38 and the outlet port 46. In one aspect, when suction is applied to the outlet port 46 upon completion of a specified sampling period, inlet air may be routed from the inlet port 39 through the inlet area 40 and into the cavity 38, and then through the fluidic manifold system to exit through the outlet area 42 and outlet port 46. Although it should be understood that other suitable geometries can be used, as shown in one aspect, the inlet area 40 may be tapered, spanning from the inlet port inward towards the cavity 38 and increasing in cross-sectional area. The outlet area 42 may be tapered, spanning outward towards the outlet port 46 and decreasing in cross-sectional area. As detailed below, this geometrical arrangement may assist the concurrent extraction and removal of desorbed analyte(s) from various regions of the cavity 38 when used with strategically placed conduits 44 of a manifold system.

An integral heater or heating unit 48 may be provided on an underside of the cavity floor 50 for thermally desorbing VOCs from an adsorbent collection material 52 that were collected in the passing gas-vapor analyte sample. In various aspects, the heating unit 48 may include a compatible heating element, such as titanium/platinum (Ti/Pt), in thermal communication with the cavity 38. For example, a heating element may be deposited on an exterior region of the bottom layer 36, such as an underside of the cavity floor 50, in direct thermal communication with the cavity 38. The heating unit 48 may be configured to heat the cavity 38, as well as its contents, to a temperature of greater than about 150° C., greater than about 200° C., or greater than about 250° C. in order to provide rapid desorption. As will be discussed, such a heating unit 48 may be able to heat the cavity 38 to such a temperature in less than about 2 seconds, less than about 1 second, less than about 0.5 seconds, or less than about 0.25 seconds, while using less than about 5 watts of power, or in some aspects less than about 1 watt of power.

It should be understood that the preconcentrator/injector device 20 of the present technology may be used to monitor VOCs in moderately complex mixtures. The passive sampling of VOCs by the device 20 is based on the physisorption of the vapor molecules at the adsorbent surface. The mechanism of physisorption involves weak interactions between the gas molecule and the solid surface by means of the Van der Waals force. The physisorbed vapor molecules can be rapidly desorbed by increasing the surface temperature. Raising the internal (i.e., vibrational) energy of the molecules results in breaking the weak bonds.

One particular challenge includes maintaining high chromatographic separation resolution. A relatively short microcolumn length may be susceptible to adverse effects by irregular elution peak shapes. Peak broadening and tailing are shape irregularities that may reduce the GC separation resolution. The heating rate of the cavity 38 may influence the injection peak band broadening. A higher heating rate may be desirable for a peak intensity enhancement. However, there may also be an upper limit for the heating rate to minimize and/or prevent the preconcentrator/injector device 20 from breaking down due to a thermal shock. Additionally, the vapor release/injection performance is affected by the kinetics of the thermal desorption of compounds trapped in the preconcentrator/injector device 20. As further discussed in Example sections below, it has been established that decreasing the heating rate by about 20% from what may be an optimal rate of about 90° C./s may cause about a 340% increase in peak tailing as well as 70% peak broadening (30% peak height reduction) to the microscale vapor injection process.

A compatible voltage source (not specifically shown) may be provided configured to apply a voltage across the heating unit 48 of equal to or less than about 12.5 volts, for example, less than about 6 volts, or less than about 1.5 volts. In various aspects, the voltage source may be portable, such as a battery housed at a suitable location within or external to the preconcentrator/injector device 20. In other aspects, there may be an external or wired voltage source.

Figure 3:
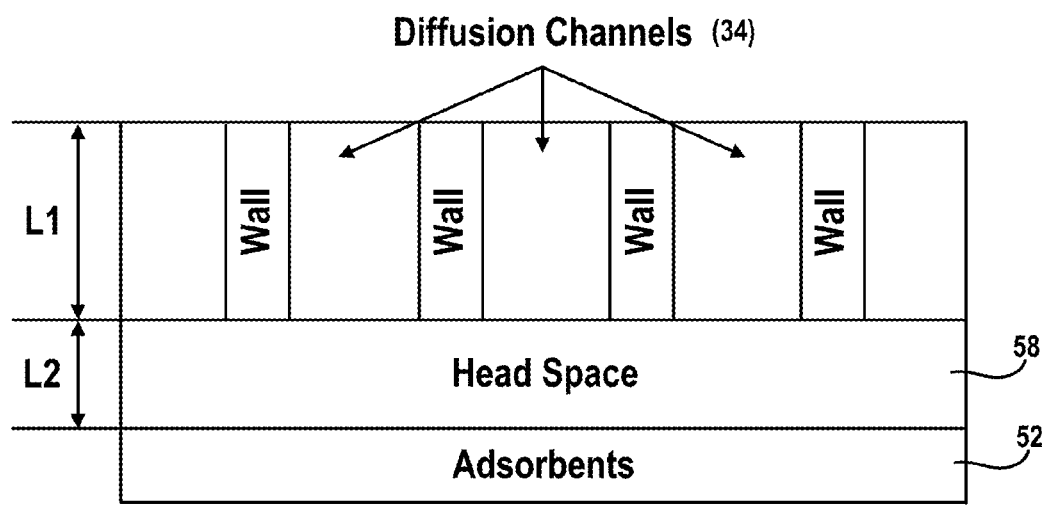
FIG. 3 is a simplified partial cross-sectional interior view of the micro-scale passive vapor preconcentrator/injector device according to various aspects of the present technology.

With reference to FIGS. 2A, 6A, and 6B The bottom layer 36 may include one or more filling or loading ports 54 for transferring various reusable collection material 52 into and out of the preconcentrator/injector device 20 as will be described below. The preconcentrator/injector device 20 may include a plurality of retention members 56 or retention structures, for example, pillars and walls configured to retain the collection material 52 within the cavity 38 and preventing escape through the manifold and outlet port 46. In one aspect, a series of retention members 56, such as pillars, may be etched in the bottom layer 36. As shown, the retention members 56 may be parallel to one another and appropriately spaced apart based on the size of the collection material 52. Other configurations, such as staggered retention members 56, may also be used. As best shown in FIG. 3, an appropriate head space 58 may be provided disposed between the collection material 52 in the cavity 38 and the grid array of micro-scale diffusion channels 34. The head space 58 may be appropriately sized based on various fluid flow properties, including the desired sampling rate and flow through the device 20 during injection to a measurement device.

In certain aspects, the passive type sampler device 20 of the present technology relies on the diffusion of vapors down a concentration gradient created within the device 20 by placing an adsorbent trap at the end of a stagnant chamber or cavity that is open to the ambient. Assuming that the air concentration is effectively zero at the surface of the trap, the diffusional sampling rate is given by the following equation, derived from Fick's first law of diffusion:

$$S = \frac{DA}{L} = \frac{m}{Ct} \qquad \text{Equation (1)}$$

where D is the diffusion coefficient of the vapor (cm$^2$/s), A is the cross-sectional area of the sampler (cm$^2$), L is the length of the diffusion path within the sampler (cm), C is the ambient vapor concentration (μg/cm$^3$), and m is the mass of vapor captured (μg) over the sampling time, t(s).

In the absence of turbulence, S is directly proportional to A and inversely proportional to L, and it is theoretically possible to scale down the size of the sampler while keeping S constant by maintaining a constant L/A ratio.

At low vapor concentrations and sub-monolayer coverage of the adsorption sites on the trapping/collection material, the amount of vapor adsorbed to the surface of a granular adsorbent at equilibrium is proportional to the air concentration of the vapor. It can be expressed as the equilibrium adsorption capacity, $W_e$, which is the ratio of the mass of adsorbed vapor to the mass of adsorbent material. As a monolayer is approached, $W_e$ no longer increases in proportion to the air concentration of the vapor, and at a full monolayer $W_e$ reaches a constant value. In the sub-monolayer regime, the adsorbent serves as an effective vapor trap and the concentration of vapor near the surface can be assumed to be close to zero, so that the sampling rate is governed by Equation (1), above. As the sites on the adsorbent gradually become occupied, the trapping efficiency is expected to decrease along with the sampling rate. The point at which the sampling rate decreases significantly is a function of time and the vapor concentration, and it defines the effective capacity or service life, as detailed below.

If used with an adsorption collection material, once the sampling period is concluded it is necessary to desorb the captured vapors for analysis. For a microfabricated device 20 of the present technology, this can be done thermally by heating the adsorbent 52 in situ and drawing the released VOCs to downstream components by means of a small pump 28 as shown in FIG. 1. Designing the device 20 for power-efficient heating may therefore be important. In addition, sufficient suction flow velocity must be provided to overcome the back-diffusion velocity imparted to the VOCs by the heating process so they do not escape through an inlet aperture, such as the grid array of micro-scale diffusion channels 34. As such, the material properties, fluidic paths, dimensional constraints, heat transfer efficiency, and velocity profiles related to these design and operating variables must all be accounted for in order to realize a viable micro-scale device suitable for use in the quantitative analysis of VOCs.

FIG. 1, described above, illustrates a block diagram layout of a micro-scale GC (μGC) system that incorporates the preconcentrator/injector device 20 as a vapor capture device. As shown, a focuser 22 is included because the pump-driven flow rate required for delivering desorbed samples from the preconcentrator/injector device 20 to the microcolumn 24 may exceed the maximum flow rate typically used in μGC separations (i.e., less than 5 mL/min). Although splitting the flow downstream from the preconcentrator/injector device 20 could be considered, a properly configured focuser 22 can function as an efficient VOC trap at relatively high flow rates and then be heated rapidly to inject a VOC sample at a lower flow rate more compatible with efficient chromatographic separations. The injected mixture of VOCs may then be separated in the microcolumn 24 and detected by an array of micro sensors 26.

Figures 4A, 4B:
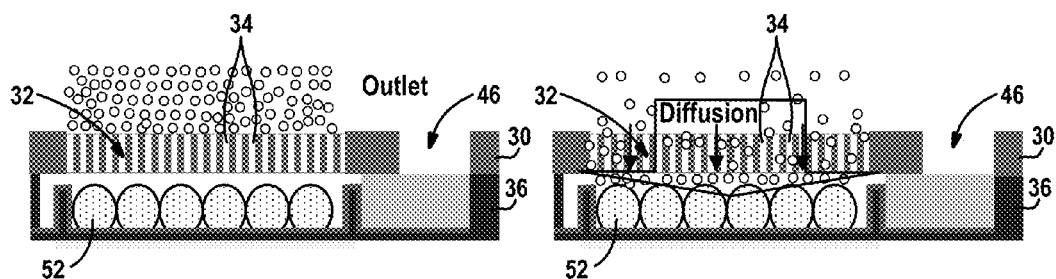
FIGS. 4A-4E illustrate exemplary sampling and desorption processes from cross-sectional views taken along the line A-A' of FIG. 2B at various steps, i.e., pre-operation (FIG. 4A), diffusion (FIG. 4B), adsorption (FIG. 4C), desorption with a heater on (FIG. 4D), and desorption with a suction pressure (FIG. 4E)
Figures 4C, 4D:
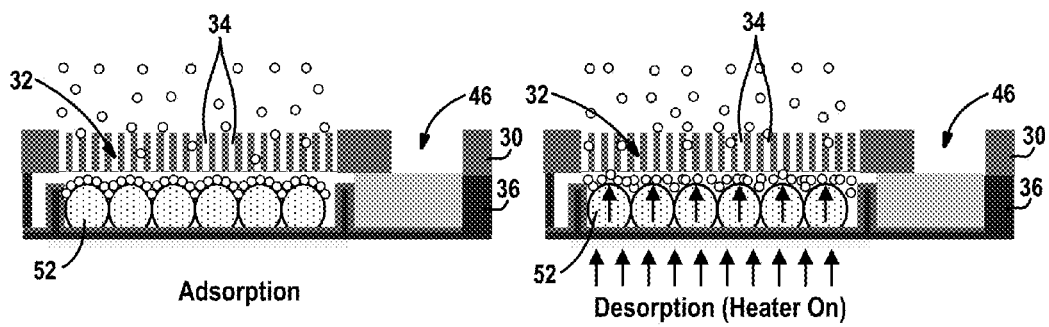
Figure 4E:
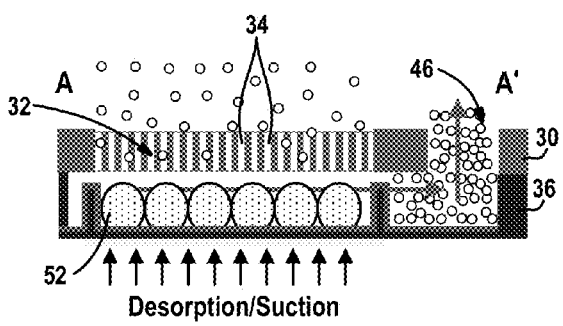

FIGS. 4A-4E detail exemplary sampling and desorption processes taken along the cross-sectional line A-A' showing particle 31 movement at various steps, i.e., pre-operation (FIG. 4A), diffusion (FIG. 4B), adsorption (FIG. 4C), desorption with a heater on (FIG. 4D), and desorption with a suction pressure (FIG. 4E). For example, as shown in FIGS. 5A-5B, the top layer 30 may contains a grid of square diffusion channels through which vapors pass into the device 20. This top layer 30 may also have a through-hole, or outlet port 46 used for fluidic interconnection to downstream components upon thermal desorption/injection of capture VOC samples. As shown in FIGS. 6A-6B, which are top plan views of the bottom layer 36, the bottom layer 36 may define a cavity 38 with tapered entrance and exit pathways 40, 42 on two opposing sides and a set of walls and pillar-shaped retention structures 56 to retain the adsorbent granules in its central region. As shown, the general area of this central region matches that of the diffusion-channel grid in the top layer 30. As shown in FIG. 6C, which is a bottom plan view of the bottom layer 36, the underside of the membrane floor 50 of the cavity 38 may be provided with an integral heating unit 48, such as a meander-line type metal thin-film heater and a resistance temperature device (RTD) for thermal desorption. The desorbed vapors are drawn through the outlet port 46 and injected onto the downstream focuser 22 as referenced in FIG. 1.

With renewed reference to FIG. 3, an exemplary thickness $L_1$ of the top layer 30, which defines the diffusional path length through the grids, can be between about 50 μm to about 500 μm, or from about 100 μm to about 300 μm, or about 200 μm. The aperture of each channel in the diffusion-channel grid can vary depending on the desired flow rate. In one aspect, the dimensions can be set at about 54 μm×54 μm, with grid walls provided about 12 μm wide. In one example, as shown, the grid can be viewed as a rectangular subsection with dimensions of 3.2 mm×1.7 mm and a trapezoidal subsection with dimensions of 3.2 mm (long side), 1.8 mm (short side), and 0.7 mm (width), the sum of which contains more than about 1,500 channels with an overall area, $A_1$, of 4.5 mm².

It should be noted that the need for a turbulence barrier may arise if the ratio of L/d is less than about 2.5, where d is the diameter of the sampling aperture. Below this value of L/d, the path length can be effectively reduced in windy environments by eddy currents created at the entrance to the sampler, to an extent that increases the sampling rate significantly. For an effective grid aperture diameter of 61 μm (derived from a circle having the same area as each grid-aperture square described above), the value of $L_1/d$ for each channel in the device is 3.3, and the effects of turbulence should be negligible.

As shown in FIG. 3, the cavity 38 in the bottom layer 36 may be designed with a small head space 58 volume above the adsorbent layer to facilitate adsorbent material 52 loading and the subsequent capture of desorbed vapors. Since vapors must diffuse through this gap, it affects the sampling rate. In one example, for a selected bottom layer substrate thickness of about 250 μm, the cavity floor thickness may be provided with a thickness of about 24 μm (via a boron-doping level, considering mechanical strength, thermal isolation, and heat transfer as discussed below) to give a cavity depth of 226 μm. The adsorbent granules may be sieved to provide a nominal average diameter of from about 150 μm to about 250 μm, or about 200 μm, depending on the chosen design parameters. Assuming spherical particles, the characteristic length (thickness) for a single-layer adsorbent bed is 161 μm. This results in an effective diffusional path length through the headspace, $L_2$, of 65 μm. The cross-sectional area of the headspace, $A_2$, is 6.7 mm² (note: $A_2$ is larger than $A_1$ because of the lack of any grid walls in the headspace).

Given the serial flow resistance through the grid and then the headspace (it should be noted that diffusion into the interstitial spaces between particles is ignored), the effective sampling rate, $S_e$, with reference to FIG. 3, can be estimated as follows:

$$S_e = D \frac{A_1 A_2}{A_1 L_2 + A_2 L_1} \quad \text{Equation (2)}$$

By way of example, using the values of the variables given above and a value of D=0.0849 cm²/s (2° C.) for toluene, Equation (2) yields an expected sampling rate of 9.3 mL/min for the μPPI device.

Various adsorbent materials 52 can be used with the present teachings, and should be selected based on the desired use of the sampling device. For example, graphitized carbon, Carbopack X ("C-X"), can be used as the adsorbent material because it may have a high affinity for toluene (and other similarly volatile VOCs), while also allowing efficient thermal desorption. This material also has a low affinity for water vapor. By way of example, the amount of C-X that can be packed into the device 20 with the above dimensions can be estimated to be about 680 μg-750 μg on the basis of the cavity volume and the published packing density for 60/80 mesh C-X of 0.41 g/cm³. Since the $W_e$ value for toluene at 1 ppm on C-X is 2800 μg/g, the capacity of the device is 2.1 μg of toluene. At 9.3 mL/min, saturation would be expected after about 60 minutes of exposure. Since $S_e$ is expected to decline prior to this point, the maximum time between successive thermal desorption/regeneration cycles should be somewhat less than this value.

The design factors that should be considered with respect to the desorption of VOCs from the μPPI device include the heating rate and power, and the air velocity required to capture (inject) the desorbed vapors. A target maximum desorption temperature of about 250-300° C. may be selected on the basis of known compatibility. A membrane floor thickness of about 24 μm for the cavity may represent compromise between minimizing thermal mass, which promotes rapid, low-power heating, and maximizing mechanical rigidity, which reduces stress-induced deflection and increases the robustness of the overall structure. In various aspects, the bottom layer 36 may comprise a low thermal conductivity material, such as silicon. Although the high thermal conductivity of p-doped Si (about 150 W/mK) promotes the rapid distribution of heat from the underlying heater to the entire adsorbent bed, it demands thermal isolation from the surrounding substrate. Therefore, a 15 μm layer of SiON (thermal conductivity=5 W/mK) may be deposited beneath the cavity floor membrane and the perimeter of the Si membrane may be removed so that the cavity floor is suspended on the SiON. A combination of lateral wall structures and arrays of pillars may be beneficial at the edges of the Si membrane to retain the adsorbent within the heated region. In the case of the latter there may also be a need to allow airflow to pass with minimal flow resistance. In one example, a Ti/Pt meanderline type heater was patterned on the underside of the SiON to enable the uniform heating of the cavity and precise, programmable temperature control with low power. In one example, thermal modeling, which accounted for the thermal contact resistance of the adsorbent layer and the convective cooling from the airflow during thermal desorption, indicated that about 1 W of power would raise the membrane temperature to about 300° C. in about 3 s and that the adsorbent bed temperature would be within a targeted range.

With respect to the fluidic factors and Equation (2), one issue to consider is the temperature dependence of D, which varies as the square of the temperature ratio, $T_2/T_1$, where $T_1$ is the reference temperature and $T_2$ is the desorption temperature. For toluene, this leads to a D value of 0.31 cm$^2$/s at 300° C. Assuming the flux out of the device is governed entirely by back diffusion, the expected volumetric flow rate upward during desorption, by Equation (2), is 34 mL/min, which corresponds to a linear velocity through the headspace of 0.1 m/s.

In one aspect, the suction flow velocity required by the downstream pump to avoid loss of desorbed vapor through the diffusion-channel grid can be estimated using CFD analysis (CFD-ACE, ESI Group, Paris, France). A CFD analysis considers the cavity dimensions, the inlet/outlet port locations and the transition geometries, and may initially assume that the entering flow comes from the inlet 39 and the grids 34 and the exiting flow went only through the outlet port 46. In various aspects, the ambient air is directed from the inlet port 39 over the heated cavity 38 and to the manifold system, thereby minimizing or preventing the escape of desorbed gas or vapor via the micro-scale diffusion channels.

Simulated flow patterns and trajectories can be examined as a function of applied suction pressure, taking into account both the forced convection by the airflow and the back-diffusion of the desorbed vapor. Criteria used to determine performance may include the presence of any points where the vertical (z-direction) velocity was positive at an elevation corresponding to the top surface of the grid, and the number and locations of stagnant loci or vortices indicative of low fluid motion within the interior cavity zone. To keep the computational task reasonable, the presence of the adsorbent granules may be ignored. It should be noted that it can be shown that the empty cavity represents a more conservative constraint in terms of preventing the vapor loss due to the back diffusion.

Figure 7A:
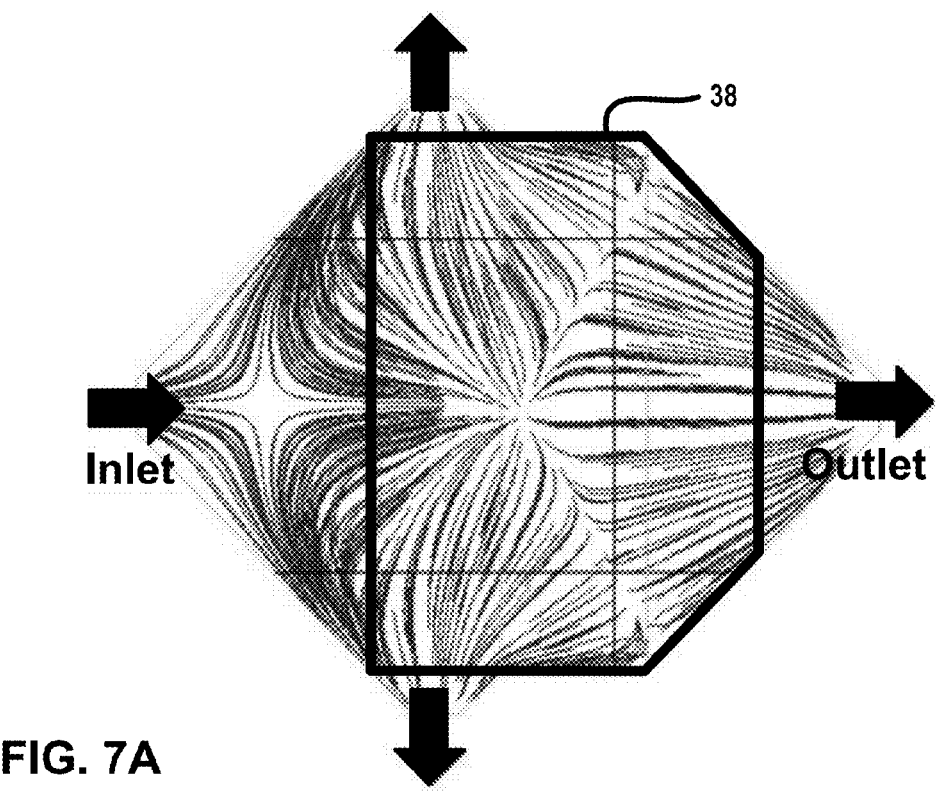
FIGS. 7A-7B illustrate velocity fields of the vapor sample during thermal desorption according to various aspects of the present technology.
Figure 7B:
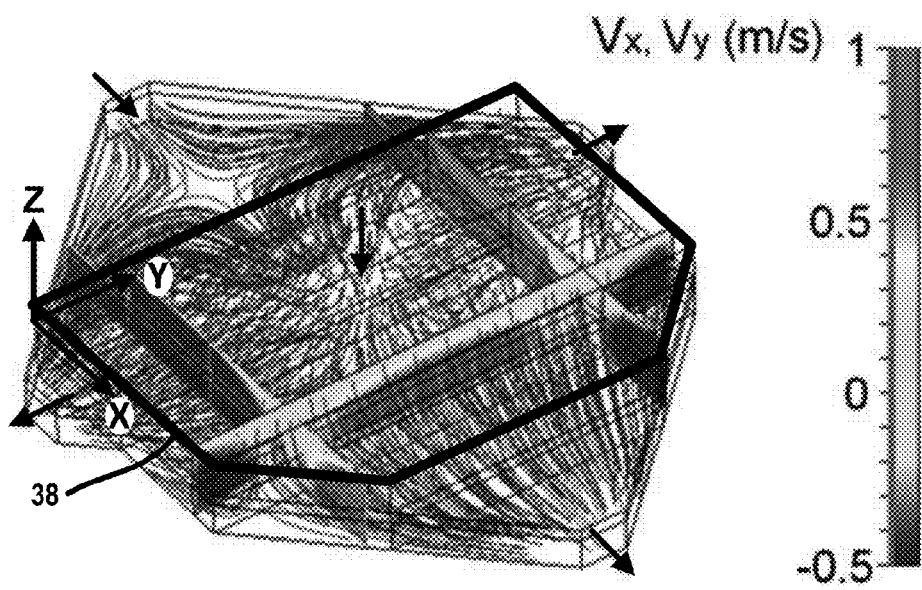
Figure 8A:
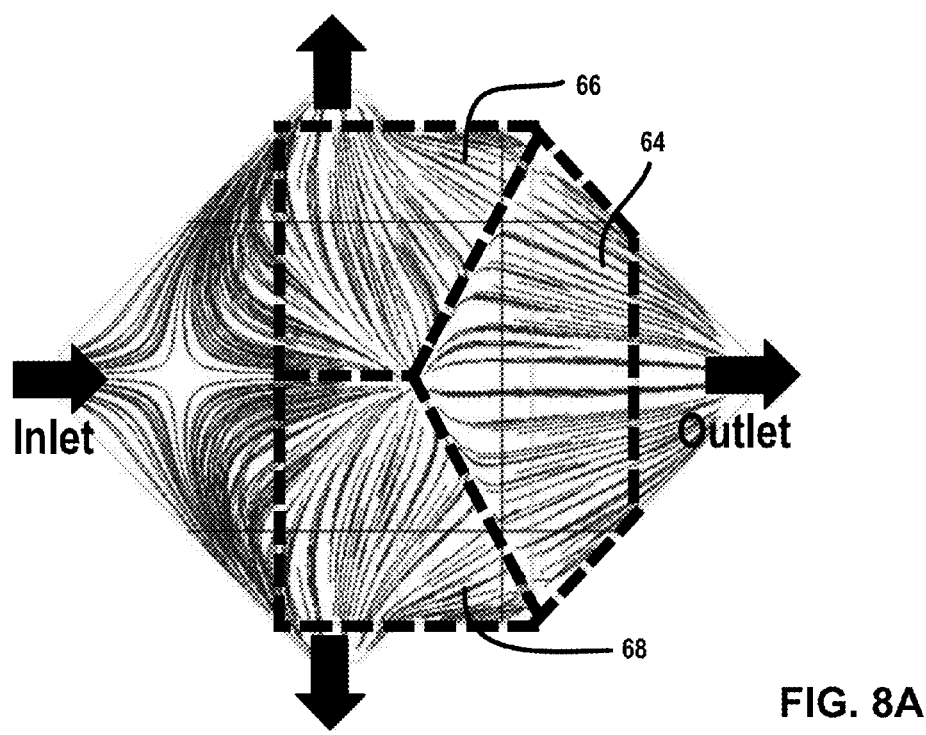
FIG. 8A illustrates three regions of the velocity fields of FIG. 7A.
Figure 8B:
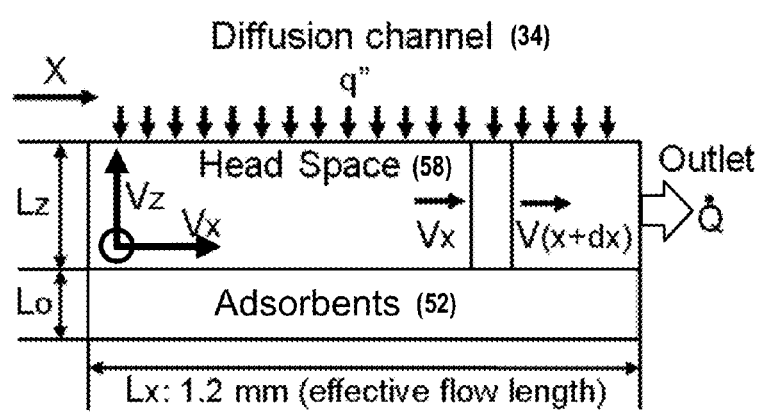
FIG. 8B illustrates a simplified cross-sectional view of the characteristic flow region within the cavity of a micro-scale passive vapor preconcentrator/injector device according to various aspects of the present technology.

FIGS. 7A-7B illustrate various velocity fields of the vapor sample through the cavity 38 during thermal desorption according to various aspects of the present technology. FIG. 7A provides a velocity field of all vapors flowing inside the cavity 38 from the inlet and the top diffusion channels divided into three regions 64, 66, 68, shown in FIG. 8A, close to the outlets. The conduits of the manifold system may include ports to particularly withdraw vapor from each region. FIG. 7B provides flow patterns inside the device cavity and distribution of velocity magnitude on cross sections normal to the outlet flows. FIG. 8B provides a simplified cross-sectional view of the characteristic flow region of the cavity, which may be used for a model to predict the capture/transfer efficiency as a function of the suction flow rate as shown in FIG. 14.

As discussed above, the tapered inlet area 40 and outlet area 42 transitions may be used to promote the uniformity of the flow profile across the width of the cavity 38, and adding optional side port 62 exit paths and conduits toward the upstream end of the cavity 38 may ensure that the vertical velocity remain negative in this region. A minimum pressure drop of 15 kPa between the inlet and the outlet may be required to avoid loss of vapor through the top-layer grid and to eliminate vapor stagnation in the cavity. This pressure drop translates into a minimum flow rate of about 60 mL/min (1.25 m/s).

EXAMPLES

In one example, the device 20 can be fabricated to include a 1.8 µL deep reactive-ion-etched (DRIE) Si cavity with a resistively heated membrane floor and a DRIE-Si cap containing greater than 1500 parallel diffusion channels, each about 54×54×200 µm in dimensions. The cavity can be packed with about 750 µg of a commercial graphitized carbon adsorbent. Fluidic and heat-transfer modeling can be used to guide the design process to ensure power-efficient sample transfer during thermal desorption. Experiments performed with toluene at concentrations of about 1 ppm give a constant sampling rate of 9.1 mL/min for up to 30 min, which is within 2% of theoretical predictions and corresponds to a linear dynamic mass uptake range of about 1 µg. The cavity membrane can be heated to 250° C. in about 0.23 seconds with 1 W of applied power and, with 50 mL/min of suction flow provided by a downstream pump, yielding greater than 95% desorption/injection efficiency of toluene samples over an 8-fold range of captured mass.

Figure 9E:
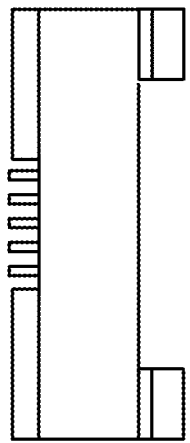
FIGS. 9A-9F illustrate an exemplary fabrication process for the top layer of micro-scale passive vapor preconcentrator/injector device according to various aspects of the present technology.
Figure 9F:
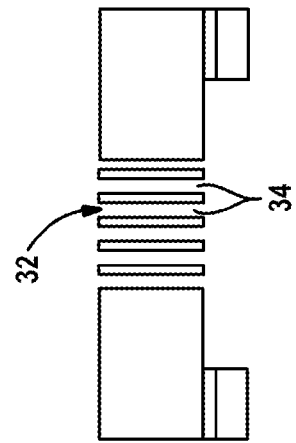
Figure 9C:
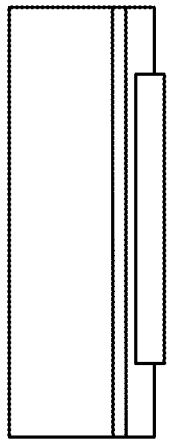
Figure 9D:
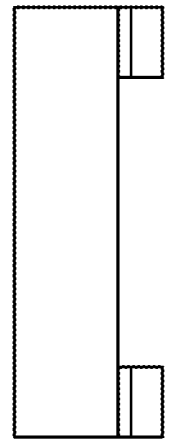
Figure 9A:
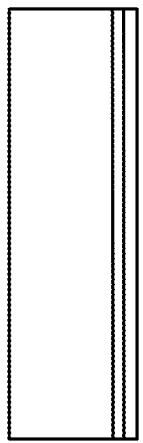
Figure 9B:
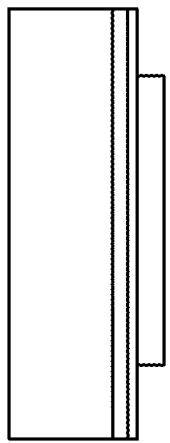

Wafers of p-doped (100) Si, 200 µm and 250 µm thick, may be used to fabricate the top and bottom layers 30, 36 of the µPPI device 20, respectively. The top layer 30 can be double-side polished and the bottom layer 36 may be single-side polished. In fabricating the top layer 30 as generally shown in FIGS. 9A-9F, a Cr/Au (10/450 nm) layer is first evaporated onto the backside and the grid wall pattern may be defined with photoresist (FIGS. 9A, 9B). Au may then be electroplated to a thickness of 3-4 µm on the perimeter of the backside of the top layer for subsequent eutectic bonding (FIG. 9C). After stripping, a new photoresist layer can be patterned to expose the grid apertures and the thin Cr/Au layers are removed by wet etching (FIGS. 9D, 9E). Through-wafer deep reactive ion etching (DRIE) may be used to create the diffusion grid 32 with channels 34 and the outlet port 46 (FIG. 9F).

The bottom layer fabrication, as generally shown in FIGS. 10A-10I, may start with the growth of a 15 µm thick thermal oxide layer on the backside of a wafer (FIG. 10A), which is then patterned (FIGS. 10B-10D) to permit formation of the pillar retention members (height: 170-190 µm; width: 90 µm; spacing: 100 µm), the lateral wall retention members (height: 170-190 µm; width: 130-440 µm), the side ports (width: 780 µm), and the side-port flow channels (height: 250 µm; width: 260 µm) by DRIE. After that, the oxide layer is stripped. A 24 µm thick boron-doped Si layer may then be formed on the backside of the cavity floor by a standard boron diffusion process for about 17 hours (FIGS. 10B-10D). A 15 µm thick low-stress SiON layer can be deposited on the backside by plasma-enhanced chemical vapor deposition (PECVD) (FIG. 10E). The Ti/Pt meander-line heater and a resistive temperature sensor is then patterned and deposited on the oxy-nitride layer by a lift-off process, followed by annealing at about 400° C. to relieve thermal stress. A Ti/Au mask layer can be deposited and patterned on the front side of the bottom layer for eutectic bonding and DRIE may be used to complete the formation of the cavity-floor membrane, filling ports, inlet, and pillars (FIGS. 10E-10H). Finally, etching in ethylenediamine-pyrocatechol (EDP) removes residual undoped Si (FIG. 10I).

The top layer 30 and bottom layer 36 structures can be diced, aligned, and temporarily fixed to each other using a small amount of epoxy (Durapot 865, Cotronics, N.Y.). This may be followed by eutectic bonding of the two layers at about 330° C. for 12 hours. In one aspect, the device 20 can be fixed to a set of pins on a small section of a printed circuit board (PCB) and an integral heater 48 and the RTD on the bottom layer 36 can be wire bonded to traces on the PCB. A capillary connector with right-angle circular channels can be fashioned from a piece of Macor® and bonded to the outlet port in the top layer using epoxy (Duraseal 1531, Cotronics, Brooklyn, N.Y.). A section of a deactivated fused-silica capillary (i.d.: 530 µm) can be inserted and sealed with the same epoxy.

A sample of 60/80 mesh C-X (having a specific surface area of 250 $m^2$/g, Supelco, Belafonte, Pa.) can be sieved to isolate granules in the size range of 180-212 µm, and then loaded into the device cavity via the loading ports under gentle suction pressure. Visual inspection can be used to confirm a single layer filling the entire cavity has been achieved. Using the above parameters, pre- and post-weighing of the device on an electronic balance indicated that about 750 µg of C-X is loaded.

Performance Testing

Test atmospheres of toluene vapor may be generated dynamically by passing $N_2$ through a fritted bubbler containing the liquid solvent and then diluting in a metered flow of dry air. A portion of the flow may be diverted every 5 minutes to a gas sampling loop mounted on a bench scale GC equipped with a flame ionization detector (FID) (Model 6890a, Agilent, Wilmington, Del.) for confirmation of the toluene concentration. The FID can be calibrated by autosampler syringe injections of liquid standards of toluene in $CS_2$. Injected masses can range from 0.4 ng to 2.2 µg and a plot of peak area vs. mass injected (i.e., calibration curve) is linear ($r^2>0.999$).

In one example, as part of a preliminary assessment of µPPI performance, the device may be placed in the weighing chamber of a thermogravimetric analyzer (TGA) (Pyris 1, Perkin Elmer, Waltham, Mass.) and exposed to toluene. The µPPI may be suspended from the weighing pan by a fine wire, and the $N_2$ purge line normally used to maintain an inert atmosphere within the semi-enclosed chamber can be modified to permit switching from $N_2$ to a test atmosphere of toluene in $N_2$. The mass of the µPPI can be recorded as a function of time to monitor toluene uptake in triplicate.

To characterize the sampling rate and desorption/injection efficiency of the device more thoroughly, the PCB-mounted µPPI can be placed inside a custom-made 25 mL environmental chamber in a system shown schematically in FIGS. 11A-11C. A flow divider at the inlet to the chamber can distribute an incoming flow (0.1 L/min) evenly over the raised device-mounting pedestal, and a portion of the exhaust flow can be directed to a 250 µL sample loop mounted on a 6-port valve. The loop may be alternately filled and then purged/injected into the GC inlet port (using a separate $N_2$ tank) in order to verify the test-atmosphere concentration (FIG. 11A). Following collection of a sample by the µPPI, the loop may be replaced with a C-X-packed focuser (described below), the upstream end of which can be connected to the Macor® connector on the outlet port of the device via a deactivated fused silica capillary (sealed within one of the chamber exit lines), and the downstream end of which can be connected via the 6-port valve, to a mini-pump (N86KNDCB, KNF Neuberger, Trenton, N.J.) (FIG. 11B). During thermal desorption/injection of the µPPI sample, the mini-pump draws $N_2$ through the device and then the focuser. The valve is then switched and the focuser can be heated rapidly and a separate $N_2$ tank may be used to backflush the toluene desorbed from the focuser to the GC column (FIG. 11C). The mass of toluene injected can be determined from the FID peak area by comparison with a calibration curve (i.e., previously generated). Replacement of the focuser with the sample loop and collection of an additional sample allows the chamber concentration to be checked post-exposure for residual toluene.

The focuser can be a stainless steel tube (0.318 cm i.d.) packed with 5 mg of C-X (sieved to about 200 µm in diameter) held in place with a wire mesh and silanized glass wool. It can be pre-conditioned initially at about 300° C. for 12 hours under $N_2$. The focuser is wrapped with an insulated Cu heater wire and thermally desorbed at 300° C. for 10 minutes, which serves to transfer the toluene to the GC and re-condition the adsorbent for subsequent samples. The capacity of the focuser can be verified in a separate series of tests showing that the mass of toluene captured and transferred to the GC matched that expected to be within 1.5%.

The PCB-mounted device can be placed on a pedestal in the center of the exposure chamber, electrical and fluidic interconnections established, and the chamber sealed and then purged with $N_2$. The system can be programmed for repeated heating and cooling tests using LabView. The device can be preconditioned at about 300° C. for 4 hours. A constant concentration of 1 ppm of toluene vapor can be passed through the chamber continuously and the device is allowed to collect samples for discrete periods of 5, 10, 15, 20, 30, 40, 50, or 60 min. This concentration can be considered relatively low for industrial working environments and relatively high for typical office or residential environments. It should be noted, however, that it may be a convenient concentration level to use because stable test atmospheres are generated easily and the sampling times required to accumulate quantities of toluene above the detection limit of the FID are not excessively long.

Tests can be run in triplicate for each time period. Following each exposure, the chamber can be purged for about 3 min with 0.11 L $min^{-1}$ of $N_2$ to remove any residual vapor. Then, the flow of $N_2$ through the chamber can be stopped and the device is rapidly self-heated to about 300° C. for about 3 minutes to desorb the captured toluene. Prior to heating, a Tedlar bag filled with $N_2$ can be connected to the chamber in order to provide make-up gas. The mini-pump can be activated to draw the desorbed toluene through the device outlet port and the focuser for 6 minutes at a flow rate ranging from 10 to 50 mL/min (note: 50 mL/min can be the default flow rate used for all experiments except those designed to examine the effect of varying flow rate on capture/injection efficiency). The 6-port valve may then be actuated and the focuser heated under a flow of $N_2$ at about 1.8 mL/min to inject the captured vapor sample into the capillary column for elution and detection by the FID.

To assess the thermal characteristics of the µPPI device, the adsorbent loaded device can be cycled between the ambient temperature and the target desorption temperature (300° C.) by repeatedly applying a constant bias of 12.5 V to the heating unit for 10 s and allowing it to cool for 190 s, with air flowing through the device. For the 140Ω baseline resistance of the meander line heating unit, this corresponds to an average of about 1.1 W of dissipated power. FIGS. 12A and 12B show a series of temperature response profiles indicating that the floor of the cavity reaches about 250° C. within 0.23 s, and 300° C. within 3 s. If the thermal cycling is continued for 100 hours, corresponding to about 2000 cycles, the time to reach the maximum temperature may be varied by less than 10% and the minimum and maximum temperatures varied by less than 3%. The power dissipation, thermal response, repeatability, and robustness exhibited by the device are all quite satisfactory.

Gravimetric Estimation of Sampling Rate

Preliminary tests of the sampling rate performed with the TGA apparatus may entail continuous exposure to about 1.2 ppm of toluene for 60 min while monitoring the mass uptake. Equation (1), discussed above, is used to estimate S. Following a few minutes of induction, the mass uptake may increase roughly linearly with time up to 24 min and then taper off significantly. Fluctuations in the TGA output signal, which can be attributable to flow-induced vibrations of the wire-suspended device, may be significant. Applying a 120-pt running average to smooth the data, followed by linear regression ($r^2$=0.967) yields a value of S=9.8±0.49 mL/min from the slope of the line. This is 5% higher than the aforementioned theoretical value of 9.3 mL/min. The total mass uptake for the linear portion of the curve is 0.86 µg, which is 45% of the total capacity of 2.1 µg. Given the mass resolution limitations of the TGA, the precision with which the slope and linear range can be estimated is limited. However, these results confirm a linear mass uptake period followed by a reduction in that rate as the fraction of occupied adsorption sites becomes large, in this case roughly 45% of the total predicted on the basis of the measured $W_e$ value.

Chamber Tests of Sampling Rate and Desorption/Injection Efficiency

Subsequent tests, performed in the exposure chamber, afforded more accurate and precise estimates of S. FIG. 13 shows a plot of injected mass versus sampling time from 5 to 60 min. The relative standard deviation was less than or equal to 5% in all cases. Analysis of the residual toluene in the chamber headspace following each desorption leads to values ranging from 3-7% of the amount initially injected, which means that the capture/injection efficiency ranges from 93-97%. There is no apparent trend in transfer efficiency with sampled mass. These results indicate that the sampling/desorption performance of the µPPI device is reproducible not only within a given sampling time but also over the entire series of experiments.

The mass uptake rate is constant up to about 30 minutes, after which it declines, in rough agreement with the results of the TGA experiments. A value of S=9.1 mL/min is obtained from the slope of the linear region ($r^2$>0.999) of the curve after correcting for the residual mass of toluene not transferred during the initial desorption. This is only 2% lower than the theoretical prediction, and corresponds to a mass uptake rate of 34 ng/min at this concentration. The linear dynamic range of the mass uptake (i.e., up to 30 minutes) is 1.01 µg, which corresponds to 48% of the total mass expected on the basis of $W_e$ and indicates that above this level of adsorbent loading the assumption of efficient trapping by the adsorbent no longer holds. However, thermal desorption of the captured sample regenerates the device for subsequent use with no apparent degradation in performance. Beyond 30 minutes, the device continues to sample, but at a lower rate, which is expected to continue to decrease as the adsorption sites on the C-X become completely filled. At t=60 min, the mass uptake is 1.5 µg, which is 71% of the total (2.1 µg) expected on the basis of the measured equilibrium adsorption capacity, $W_e$, assuming the designed sampling rate of 9.3 mL/min.

The capture/injection efficiency during thermal desorption is then examined as a function of the suction flow rate. For each of these tests, the device is exposed to 1 ppm of toluene for 15 min, leading to an expected mass uptake of 525 ng. The device is then heated while drawing flow from the downstream minipump at different flow rates. Results, plotted in FIG. 14, show that the capture efficiency decreases at a modest rate on going from 53 to 20 mL/min and at an apparently higher rate below 20 mL/min. The high efficiency observed at 52 mL/min (i.e., 93%) is consistent with the results reported above and with predictions from CFD analysis.

To further explore this, a two-dimensional analytical model can be developed for the capture/injection efficiency of the µPPI. The 2D model derives a mathematical formulation for the ratio of the sampled mass to the mass captured (and transferred to the focuser for GC analysis) during thermal desorption as a function of the suction flow rate. As shown by the dashed line in FIG. 14, the agreement of the model with the experimental results is reasonably good, particularly at the extremes of the range tested; the experimental value of 93% efficiency at the highest flow rate of 52 mL/min is only 7% lower than predicted by the model. Notably, a flow rate greater than 10 mL/min is required to capture greater than 50% of the desorbed vapor sample, hence the need for a focuser (or split-flow adaptor) to interface with a GC (micro) column.

These results demonstrate that the µPPI device can capture VOCs from the air at low concentrations with zero power dissipation (i.e., without active pumping) at a known and predictable rate. Efficient thermal desorption using the integrated heater and near-quantitative transfer of discrete samples to downstream components (with pumping) are also demonstrated.

The sampling rate of 9.1 mL/min observed for the test vapor, toluene, is remarkably high given the size of the device. Similar rates are expected from numerous other vapors with comparable diffusion coefficients in air, independent of the VOC concentration. Thus, sufficient mass can be collected within a few minutes from environments containing low- or sub-ppm concentrations to permit detection by any of a number of downstream microsensors (following focused injection and, possibly, chromatographic separation). The time span over which a given sampling rate can be maintained is a function of the vapor concentration and its affinity for the adsorbent material packed in the device. For 1 ppm of toluene and the graphitized carbon adsorbent, Carbopack X, used in the µPPI device, sampling is maintained at a constant rate for 30 minutes prior to having to thermally desorb the sample and regenerate the adsorbent surface. Repeated sampling/desorption cycles are possible, without any apparent effect on performance. FIGS. 15A-15B illustrate the mass uptake rates measured by TGA for toluene concentrations of 1.2 ppm and 1.7 ppm, respectively using a micro-scale passive vapor preconcentrator/injector device according to various aspects of the present technology.

Effect of Thermal Desorption Kinetics on Vapor Injection Peak

After mounted on a wire-bonded printed circuit board (PCB), the µPPI device can be placed on a pedestal in the center of the exposure chamber. A flow splitter can be placed at the chamber inlets to evenly distribute the incoming carrier gas ($N_2$) flow over the µPPI device placed inside. The exhaust flow can be directed to the chamber outlet connected to the downstream GC system. After electrical and fluidic interconnections are established, the exposure chamber can be sealed. The system can be programmed to control the device temperature using the LabView (National Instruments, Austin, Tex.) program. The sealed chamber may be initially purged with $N_2$ and then filled with toluene in $N_2$, followed by the passive sampling with the μPPI device. After finishing loading the toluene sample to the μPPI device, the chamber can be re-purged to remove residual toluene vapor. A mini-pump (KNF Neuberger, Trenton, N.J.) can be operated to draw the vapor in $N_2$ through the device outlet to a focuser at a flow rate of 50 mL/min. The flow rate of 50 mL/min may be necessary to minimize the vapor loss during the vapor desorption process by the μPPI device, although it exceeds the maximum flow rate usually permitted in conventional GC separations (<5 mL/min). As a result, once can first re-capture the toluene injected from the μPPI device at the focuser and then deliver it to the flame ionized detector (FID) at a lower flow rate compatible with the GC system. One can determine the total toluene mass released from the μPPI device from the integrated signal of the FID and its calibration data. The exposure chamber may be cleaned with $N_2$ upon the completion of each desorption characterization cycle for subsequent repeated measurements.

The heating response of the μPPI device can be characterized experimentally and compared with the theoretical prediction provided by a lumped thermal model. Parameters, such as thermal conductivity of the constituent materials, the membrane thickness, and the total effective contact area between the Carbopack X layer and the cavity floor can be estimated from published data and scanning electron microscopy (SEM) images. The thermal conductivity and the thickness of the membrane affect the heat transfer rate by conduction across the membrane structure from the heater. The thermal contact resistance $R_c$ between the cavity membrane floor surface and the Carbopack X layer can be expressed as: $R_c = R''_{t,c}/A_c$, where $R''_{t,c}$ is the intrinsic thermal resistance of the interface (i.e., the reciprocal of the thermal conductance per unit area) and $A_c$ is the total effective contact area, which can be estimated to be 4500 about $\mu m^2$. The intrinsic thermal contact resistance $R''_{t,c}$ generally ranges from $10^{-7}$ to $10^{-4}$ $m^2 \cdot KW^{-1}$ for an interface between a carbon material and silicon. With the contact resistance at the Carbopack X-silicon interface unknown, the upper bound for the value of $R''_{t,c} = 10^{-4} m^2 \cdot KW^{-1}$ for the thermal equations can be used for conservative model prediction resulting in a minimum heat transfer rate.

The μPPI device can be heated for durations of 2, 3, and 5 s at 1.1 W of average dissipated power and allowed to cool for 50 s. The predicted heating responses of the cavity floor and the experimental results measured by the RTD sensor on the device membrane can both be plotted. The experimental data and the theoretical prediction are consistent with each other for all the heating durations, indicating that the temperature of the membrane floor could reach 250° C. within 0.3 s under the above conditions. The device reached the maximum temperature of 289° C., 300° C., and 315° C. for the heating duration of 2 s, 3 s, and 5 s, respectively. The heat transfer model was verified by these tests. The predicted temperature profile of the cavity floor matched the measured temperature profile with an error as small as 2%.

To avoid device 20 failure, it has been experimentally established that decreasing the heating rate by about 20% from what may be an optimal rate of about 90° C./s may cause about a 340% increase in peak tailing as well as 70% peak broadening (30% peak height reduction) to the microscale vapor injection process. From transient vapor signal profiles, the peak tailing effect can be quantified by taking the ratio of the maximum peak height to the residual peak height and comparing the experimental value to that of a theoretical curve. The decrease in the heating rate also caused a 340% increase in peak tailing (380% by theory) to the microscale vapor injection process.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A passive preconcentrator and injector device, comprising:
   an upper portion defining an array of micro-scale diffusion channels;
   a lower portion defining a cavity in fluid communication with the micro-scale diffusion channels;
   a collection material disposed within the cavity and configured to capture at least one gas-phase analyte;
   an integral heating unit disposed in thermal communication with the lower portion and configured to heat the cavity;
   an inlet port and an outlet port in fluid communication with the cavity; and
   a fluidic manifold system disposed between the cavity and the outlet port, the fluidic manifold system comprising a plurality of conduits in fluid communication with and configured to concurrently extract desorbed analyte(s) from a plurality of regions of the cavity, wherein the device is configured to collect at least one compound in a gas phase at a known rate by using passive diffusion, without the use of artificial circulation, and subsequently remove the compound for injection to a measuring device.

2. The passive preconcentrator and injector device according to claim 1, wherein the heating unit is configured to heat the cavity to a temperature of greater than about 250° C. in less than about 0.25 seconds and using less than about 1 W of power.

3. The passive preconcentrator and injector device according to claim 1, wherein the heating unit comprises a Ti/Pt element deposited on an exterior region of the lower portion in direct thermal communication with the cavity.

4. The passive preconcentrator and injector device according to claim 1, further comprising a head space disposed between the collection material in the cavity and the microscale diffusion channels.

5. The passive preconcentrator and injector device according to claim 1, further comprising a tapered inlet area, the tapered inlet area spanning from the inlet port inward towards the cavity and increasing in cross-sectional area.

6. The passive preconcentrator and injector device according to claim 1, further comprising a tapered outlet area, the tapered outlet area spanning outward towards the outlet port and decreasing in cross-sectional area.

7. The passive preconcentrator and injector device according to claim 1, further comprising a loading port for transferring the collection material into and out of the cavity.

8. The passive preconcentrator and injector device according to claim 1, the lower portion further comprising a plurality of cavities and the upper portion further comprising a plurality of micro-scale diffusion channel arrays, wherein the plurality of cavities and the plurality of micro-scale diffusion channel arrays are in respective fluid communication with one another.

9. The passive preconcentrator and injector device according to claim 1, further comprising a plurality of retention members configured to retain the collection material within the cavity.

10. The passive preconcentrator and injector device according to claim 9, wherein the retention members comprise pillars, and the device further comprises walls disposed about a periphery of the cavity.

11. The passive preconcentrator and injector device according to claim 1, wherein the micro-scale diffusion channels comprise an aperture, a depth, and a total number sufficient to provide a finite sampling rate from about 0.2 to about 20 mL/min.

12. The passive preconcentrator and injector device according to claim 11, wherein a ratio of channel depth to channel diameter of the micro-scale diffusion channels is greater than about 2.5, thereby minimizing any interference from ambient wind turbulence on the sampling rate.

13. The passive preconcentrator and injector device according to claim 1, further comprising a voltage source configured to apply a voltage across the heating unit of equal to or less than about 12.5 volts.

14. The passive preconcentrator and injector device according to claim 13, wherein the voltage source comprises a portable battery.

15. A passive preconcentrator and injector apparatus comprising a plurality of devices according to claim 1 and configured to independently sample a plurality of different compounds.

16. A passive preconcentrator and injector apparatus according to claim 15, configured for simultaneously sampling a plurality of volatile compounds.

17. A passive preconcentrator and injector apparatus according to claim 15, wherein at least two of the plurality of devices comprise different collection materials.

18. A passive preconcentrator and injector apparatus according to claim 15, wherein at least two of the plurality of devices comprise different micro-scale diffusion channel geometries.

19. A passive preconcentrator and injector device, comprising:
- an upper plate defining an array of micro-scale diffusion channels;
- a lower plate secured to the upper plate and defining a cavity in fluid communication with the micro-scale diffusion channels;
- an integral heating unit disposed on an exterior region of the lower plate and configured for heating the cavity;
- a loading port for introducing a reusable collection material;
- an inlet port and an outlet port both in fluid communication with the cavity; and
- a fluidic manifold system comprising a plurality of conduits disposed between the cavity and the outlet port.

20. A method of detecting a compound in the gas phase using a combination preconcentrator and injector device, the method comprising:
- providing a passive preconcentrator and injector device including an upper portion defining an array of micro-scale diffusion channels, a lower portion defining a cavity in fluid communication with the micro-scale diffusion channels and containing a collection material, an integral heating unit, an inlet, an outlet, and a fluidic manifold system disposed between the cavity and the outlet port, the fluidic manifold system comprising a plurality of conduits in fluid communication with a plurality of regions of the cavity;
- exposing the preconcentrator and injector device to a sampling area and allowing the collection material to passively capture a gas-phase analyte sample for a predetermined time period at a predetermined rate;
- connecting the outlet to a measurement device;
- actuating the integral heating unit and initiating thermal desorption to generate a desorbed gas or vapor; and
- collecting and analyzing the desorbed gas or vapor to detect at least one captured or desorbed compound.

21. The method of claim 20, wherein the measurement device comprises a gas chromatographic microsystem.

22. The method of claim 20, wherein actuating the integral heating unit comprises applying low voltage pulses generating heat power of less than about 1 W through the cavity.

23. The method of claim 20, comprising actuating the integral heating unit and permitting thermal desorption for a time period sufficient to remove substantially all of the collected compound(s) and rendering the device available for immediate reuse after collecting the vapor.

24. The method of claim 20, wherein collecting the vapor comprises connecting a suction pressure to the outlet and transferring the desorbed gas or vapor out from the cavity using the fluidic manifold system in fluid communication with at least three regions of the cavity.

25. The method of claim 24, comprising directing ambient air from the inlet over the heated cavity and to the fluidic manifold system, thereby minimizing or preventing the escape of desorbed gas or vapor via the micro-scale diffusion channels.

* * * * *